United States Patent [19]

Johnson

[11] 4,259,479

[45] Mar. 31, 1981

[54] 2-DECARBOXY-2-AMINOMETHYL-4-HALO-5,9-EPOXY-9-DEOXY-PGF$_1$ COMPOUNDS

[75] Inventor: Roy A. Johnson, Kalamazoo, Mich.

[73] Assignee: The Upjohn Company, Kalamazoo, Mich.

[21] Appl. No.: 73,454

[22] Filed: Sep. 7, 1979

Related U.S. Application Data

[60] Division of Ser. No. 932,981, Aug. 11, 1978, which is a division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.$^3$ .............................................. C07D 307/93
[52] U.S. Cl. ................................. 542/426; 260/345.2; 542/429
[58] Field of Search .................... 260/345.2; 542/426, 542/429, 420, 421

[56] References Cited

U.S. PATENT DOCUMENTS

| | | | |
|---|---|---|---|
| 4,125,713 | 11/1978 | Nelson | 542/426 |
| 4,158,667 | 6/1979 | Axen | 260/346.22 |

*Primary Examiner*—Nicky Chan
*Attorney, Agent, or Firm*—Robert A. Armitage

[57] ABSTRACT

The present invention relates to novel 2-decarboxy-2-aminomethyl-4-halo-5,9-epoxy-9-deoxy-PGF$_1$ compounds, which are intermediates useful for the preparation of corresponding 5,9α-epoxy-9-deoxy-PGF$_1$ and 5,9-epoxy-9-deoxy-4,5-didehydro-PGF$_1$ compounds. These end products are employed for induction of a variety of prostacyclinlike pharmacological effects. Accordingly, these end products are useful pharmacological agents for the same purposes for which prostacyclin is employed.

4 Claims, No Drawings

2-DECARBOXY-2-AMINOMETHYL-4-HALO-5,9-EPOXY-9-DEOXY-PGF$_1$ COMPOUNDS

CROSS REFERENCE TO RELATED APPLICATION

The present application is a divisional application of U.S. Ser. No. 932,981, filed Aug. 11, 1978, now pending issuance as a United States patent; which is a divisional application of U.S. Ser. No. 819,856, filed July 28, 1977, now U.S. Pat. No. 4,123,441; which is a continuation-in-part application of U.S. Ser. No. 725,546, filed Sept 22, 1976, now abandoned; which is a continuation-in-part application of United States Ser. No. 716,960, filed Aug. 23, 1976, now abandoned.

BACKGROUND OF THE INVENTION

The present invention relates to novel 2-decarboxy-2-aminomethyl-4-halo-5,9-epoxy-9-deoxy-PGF$_1$ compounds, which are intermediates useful for the preparation of corresponding 5,9α-epoxy-9-deoxy-PGF$_1$ and 5,9-epoxy-9-deoxy-4,5-didehydro-PGF$_1$ compounds. These end products are employed for induction of a variety of prostacyclin-like pharmacological effects. Accordingly, these end products are useful pharmacological agents for the same purposes for which prostacyclin is employed.

These essential material constituting a disclosure of the preparation and use of the novel compounds of the present invention is incorporated here by reference from U.S. Pat. No. 4,123,441.

SUMMARY OF THE INVENTION

The present invention particularly provides: a compound of the formula

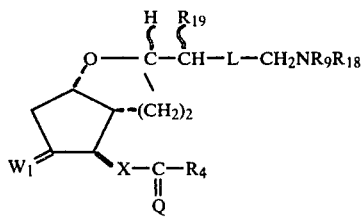

wherein W$_1$ is α-OH:β-H, α-H:β-OH, oxo, methylene, α-H:β-H, α-CH$_2$OH:β-H;
wherein L is
(1)—(CH$_2$)$_d$—C(R$_2$)$_2$—, or
(2)—O—CH$_2$—Y—,
wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is oxo, α-H:β-H, α-OH:β-R$_8$ or α-R$_8$:β-OH wherein R$_8$ is hydrogen or alkyl of one to 4 carbon atoms, inclusive,
wherein R$_9$ is hydrogen, methyl, or ethyl, and wherein R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein R$_4$ is
(1) —CR$_5$R$_6$—C$_g$H$_{2g}$—CH$_3$
(2) —CR$_5$R$_6$—Z—(Ph)
(3) cis—CH$_2$—CH=CH—CH$_2$CH$_3$
wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the (Ph); wherein (Ph) is phenyl or phenyl substituted by (T)s, wherein T is alkyl of one to 4 carbon atoms, inclusive, fluoro, chloro, trifluoromethyl, or —OR$_7$—, wherein R$_7$ is alkyl of one to 4 carbon atoms, inclusive, and s is zero, one, 2, or 3, with the proviso that not more than two T's are other than alkyl and when s is 2 or 3 the T's are either the same or different;
wherein R$_{19}$ is chloro, bromo, or iodo; and wherein X is
(1) trans—CH=CH—
(2) cis—CH=CH—
(3) —C≡C— or
(4) —CH$_2$CH$_2$—.

With regard to the divalent substituents described in the claims, e.g., Q and W$_1$, these divalent radicals are defined as α—R$_i$:β—R$_j$, where R$_i$ represents a substituent of the divalent moiety of the alpha configuration with respect to the cyclopentane and R$_j$ represents a substituent of the divalent moiety of the beta configuration with respect to the cyclopentane ring. Accordingly, when Q is defined as α—OH:β—R$_8$, the hydroxy of the Q moiety is in the alpha configuration, i.e., as in prostacyclin, and the R$_8$ substituent is in the beta configuration. Not all carbon atoms to which such divalent moieties are attached represent asymmetric centers. For example, when both valence bonds are to hydrogen (e.g., W$_1$ or Q is α—H:β—H), then no asymmetric center is present.

DESCRIPTION OF THE PREFERRED EMBODIMENTS

The present invention particularly relates to the following chemical compounds:

2-Decarboxy-2-aminomethyl-4ξ-iodo-9-deoxy-5ξ,9α-epoxy-PGF$_1$;

2-Decarboxy-2-aminomethyl-4ξ-bromo-9-deoxy-5ξ,9α-epoxy-PGF$_1$;

2-Decarboxy-2-aminomethyl-4ξ-iodo-9-deoxy-5ξ,9α-epoxy-15-keto-PGF$_1$;

2-Decarboxy-2-aminomethyl-4ξ-iodo-9-deoxy-5ξ,9α-epoxy-15-deoxy-PGF$_1$; and

2-Decarboxy-2-aminomethyl-4ξ-iodo-9-deoxy-5ξ,9α-epoxy-17-phenyl-18,19,20-trinor-PGF$_1$.

I claim:

1. A compound of the formula

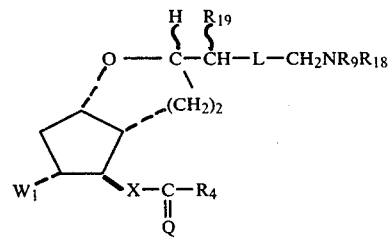

wherein $W_1$ is $\alpha$-OH:$\beta$-H, $\alpha$-H:$\beta$-OH, oxo, methylene, $\alpha$-H:$\beta$-H, $\alpha$-Ch$_2$OH:$\beta$-H;

wherein L is

—(CH$_2$)$_d$—C(R$_2$)$_2$—, wherein d is zero to 5, R$_2$ is hydrogen, methyl, or fluoro, being the same or different with the proviso that one R$_2$ is not methyl when the other is fluoro, wherein Q is oxo, $\alpha$—H:$\beta$-H, $\alpha$—OH:$\beta$-R$_8$ or $\alpha$—R$_8$:$\beta$—OH wherein R$_8$ is hydrogen or alkyl of one to 4 carbon atoms, inclusive, wherein R$_9$ is hydrogen, methyl, or ethyl, and wherein R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;

wherein R$_4$ is (1) —CR$_5$R$_6$—C$_g$H$_{2g}$-CH$_3$
(2) —CR$_5$R$_6$—Z—(Ph)
(3) cis—CH$_2$—CH=CH—CH$_2$CH$_3$ wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive, between CR$_5$R$_6$—and the (Ph); wherein (Ph) is phenyl or phenyl substituted by (T)s, wherein T is alkyl of one to 4 carbon atoms, inclusive, fluoro, chloro, trifluoromethyl, or —OR$_7$—, wherein R$_7$ is alkyl of one to 4 carbon atoms, inclusive, and s is zero, one, 2, or 3, with the proviso that not more than two T's are other than alkyl and when s is 2 or 3 the T's are either the same or different;

wherein R$_{19}$ is chloro, bromo, or iodo; and wherein X is (1) trans—CH=CH—
(2) cis—CH=CH—
(3) —C≡C— or
(4) —CH$_2$CH$_2$—.

2. A compound according to claim 1, wherein W is $\alpha$-OH:$\beta$-H.

3. A compound according to claim 2, wherein L is —(CH$_2$)$_n$—, n being 2, 3, or 4, wherein Q is oxo or $\alpha$—OH:$\beta$—R$_8$ and wherein R$_8$ is hydrogen, methyl, or ethyl, and wherein R$_4$ is n-pentyl, 1,1-dimethylpentyl, 1,1-difluoropentyl, phenoxymethyl or phenylethyl.

4. A compound according to claim 3, wherein X is trans—CH=CH—.

* * * * *